(12) United States Patent
Sailor et al.

(10) Patent No.: US 7,942,989 B2
(45) Date of Patent: May 17, 2011

(54) POROUS SILICON-BASED EXPLOSIVE

(75) Inventors: Michael J. Sailor, La Jolla, CA (US);
Frederic V. Mikulec, Austin, TX (US);
Joseph D. Kirtland, Ithaca, NY (US)

(73) Assignee: The Regents of the University of California, Oakland, CA (US)

( * ) Notice: Subject to any disclaimer, the term of this patent is extended or adjusted under 35 U.S.C. 154(b) by 836 days.

(21) Appl. No.: 10/731,220

(22) Filed: Dec. 9, 2003

(65) Prior Publication Data

US 2004/0244889 A1    Dec. 9, 2004

Related U.S. Application Data

(60) Provisional application No. 60/432,112, filed on Dec. 10, 2002.

(51) Int. Cl.
*C06B 25/00* (2006.01)
*C06B 25/04* (2006.01)
*C06B 25/32* (2006.01)
*C06B 31/00* (2006.01)
*C06B 31/02* (2006.01)
*C06B 31/12* (2006.01)
*C06B 31/16* (2006.01)
*C06B 31/28* (2006.01)
*C06B 35/00* (2006.01)
*C06B 45/00* (2006.01)
*C06B 45/04* (2006.01)

(52) U.S. Cl. .................. 149/45; 149/2; 149/17; 149/35; 149/46; 149/61; 149/93; 149/105; 149/108.6

(58) Field of Classification Search ................. 149/2, 45, 149/46, 61, 109.4; 422/78; 436/196, 199; 102/202.5
See application file for complete search history.

(56) References Cited

U.S. PATENT DOCUMENTS

| 704,409 | A | * | 7/1902 | Way | ............................. 436/80 |
|---|---|---|---|---|---|
| 3,238,074 | A | * | 3/1966 | Griffith et al. | ................. 149/38 |
| 4,705,582 | A | * | 11/1987 | Aubert | ............................ 149/92 |
| 6,170,399 | B1 | * | 1/2001 | Nielson et al. | ............... 102/336 |
| 6,220,164 | B1 | * | 4/2001 | Laucht et al. | .............. 102/202.5 |
| 6,666,935 | B1 | * | 12/2003 | Simpson et al. | ........... 149/19.92 |
| 6,803,244 | B2 | * | 10/2004 | Diener et al. | ................... 438/22 |
| 6,929,950 | B2 | * | 8/2005 | Canham et al. | .............. 435/459 |
| 6,984,274 | B2 | * | 1/2006 | Hofmann et al. | ................ 149/2 |

FOREIGN PATENT DOCUMENTS

WO    WO01/76564    * 10/2001

OTHER PUBLICATIONS

Nonintrusive Diagnostic Techniques for Research on Nonsteady Burning of Solid Propellants, Parr, Chap. 8.*
Ennis et al., On Hazardous Silver Compounds, 1991, J. Chem. Educ., 68 (1), p. A6 and A8.*
"Advanced Materials" vol. 14, No. 1, pp. 38-41, Jan. 4, 2002.
"Semiconductor bridge: A plasma generator for the ignition of explosives", D.A. Benson, M.E. Larsen, A.M. Renlund, W.M. Trott, R.W. Bickes, *J. Appl. Phys.* 62(5), Sep. 1, 1987, pp. 1622-1632.

(Continued)

*Primary Examiner* — Jerry Lorengo
*Assistant Examiner* — Jared Wood
(74) *Attorney, Agent, or Firm* — Greer, Burns & Crain Ltd.

(57) ABSTRACT

An initiator explosive for detonating a second explosive that includes nanocrystalline silicon containing a plurality of pores and a solid state oxidant disposed within said pores.

16 Claims, 1 Drawing Sheet

OTHER PUBLICATIONS

"Smart Dust: Communicating with a Cubic-Millimeter Computer", B. Warneke, M. Last, B. Uebowitz. K. S.J. Pister, *Computer*, Jan. 2001, pp. 44-51.

"Sliding spark spectroscopy—a new excitation source for generating atomic emission spectra for analysis", A. Golloch, T. Seidel, *Fresenius J. Anal. Chem.* (1994) 349: pp. 32-35.

"Spark-Gap Atomic Emission Microscopy", P.G. Van Patten, J.D. Noll, M.L. Myrick, C.R. Li, T.S. Sudarshan, J. Phys. Chem. 1996, 100, pp. 3646-3651.

"Spark-gap tomic emission icroscopy. II. Improvements in resolution", P.G. Van Patten, J.D. Noll, M.L. Myrick, *J. Vac. Sci. Technol.* B 15(2), Mar./Apr. 1997.

\* cited by examiner

POROUS SILICON-BASED EXPLOSIVE

REFERENCE TO RELATED APPLICATION AND PRIORITY CLAIM

This application is related to pending provisional application Ser. No. 60/432,112, filed on Dec. 10, 2002, and claims priority from that provisional application under 35 U.S.C. §119. Provisional application Ser. No. 60/432,112 is incorporated herein by reference in its entirety.

STATEMENT OF GOVERNMENT INTEREST

This invention was made with government support under Grant No. DMR-97-00202 awarded by the Nationl Science Foundation and Grant No. N66001-98-C-8514 awarded by the Defense Advanced Research Projects Agency (DARPA). The government has certain rights in the invention.

FIELD OF THE INVENTION

A field of the invention is explosives, and the invention is particularly concerned with small and microscale controlled explosives. Other fields of the invention including chemical sensing, microelectromechanical (MEMS) devices, and emission spectroscopy.

BACKGROUND OF THE INVENTION

Silicon is commonly the primary constituent material of most common semiconductor chip circuitry, and as a consequence, there exists a widespread interest in silicon-based technology, such as silicon-based sensors or silicon-based microelectromechanical systems (MEMS). Chemical sensors or chemosensors are small synthetic molecules that produce a measurable signal upon interaction with a specific analyte, and are used to determine the existence and/or concentration of a subject analyte without involving complicated analytical techniques or disturbance of the system being analyzed. Among other numerous uses, chemical sensors may be used for detecting explosives at security checkpoints or in the battlefield, monitoring pollutants in wastewater and quantifying contaminants in chemical compositions.

Like gunpowder, which is a mixture of carbon, potassium nitrate (i.e., saltpeter) and sulfur, porous silicon combined liquid oxygen or nitric acid with was known to combust when ignited with, for example, a flame or heat-producing impact. However, nitric acid is extremely corrosive, rendering it an unfavorable candidate as a chemical sensor in combination with silicon. Similarly, liquid oxygen lacks adequate portability for use in quick and easy on-site applications, insofar as it requires extremely low temperatures (~77K) to maintain its aqueous state. Moreover, nitric acid and liquid oxygen detonate porous silicon spontaneously on contact and must therefore be kept separate from the porous silicon and added to the porous silicon only at the instant an explosion is desired. Also, since they are liquids, nitric acid and liquid oxygen must be added to the porous silicon to obtain the explosion via dripping, injection, or other method. Liquid delivery of these oxidants therefore poses a problem inasmuch as the liquid may evaporate when stored over a long period of time, it may be difficult to deliver the liquid on cue, and it is difficult to prevent the corrosive liquid from damaging other components of the device housing the explosive.

Thus, conventional silicon-based explosives lack practical qualities that would make such explosives viable for use in chemical sensing applications, especially those that require quick analysis and portability in the field.

Conventional silicon-based sensors have drawbacks for MEMS applications as well. MEMS devices are microscale mechanical devices. For example, MEMS may integrate mechanical elements—with sensors, actuators, and electronics on a common silicon substrate through microfabrication technology. While the electronics are fabricated using integrated circuit (IC) process sequences (e.g., CMOS, Bipolar, or BICMOS processes), the micromechanical components are fabricated using compatible "micromachining" processes that selectively etch away parts of the silicon wafer or add new structural layers to form the mechanical and electromechanical devices.

BRIEF DESCRIPTION OF THE INVENTION

An initiator explosive for detonating a second explosive that includes nanocrystalline silicon containing a plurality of pores and a solid state oxidant disposed within said pores.

DETAILED DESCRIPTION OF THE INVENTION

Figure 1:
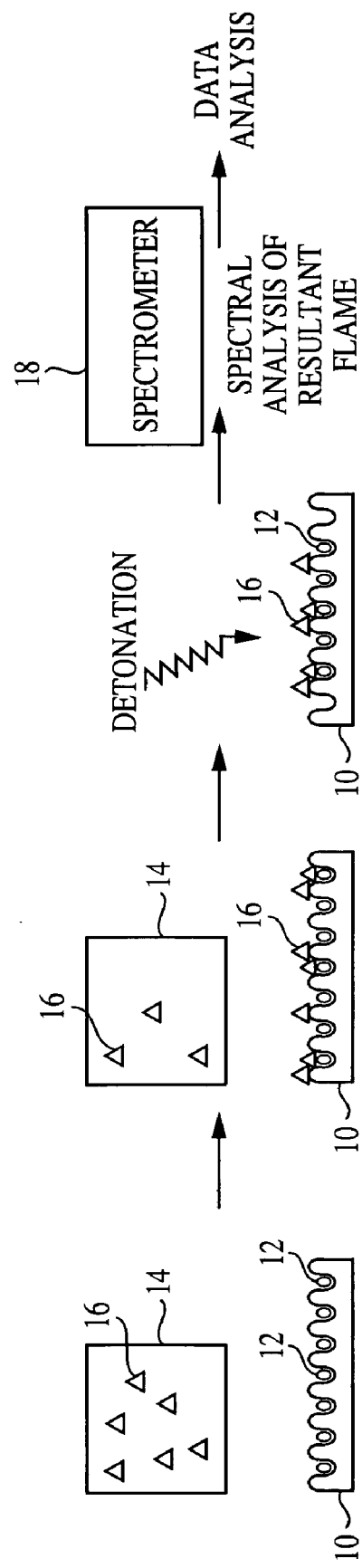
FIG. 1 is a schematic diagram of a preferred embodiment of the instant invention.

The instant invention is directed to a solid-state silicon-based explosive that may be used in a multitude of applications insofar as the explosive provides both a source of excitation (via the explosion) and a matrix for an analyte. A silicon-based explosive of the instant invention may be used to create initiating explosions that provide ignition for a larger secondary explosion. The instant invention is also useful in military, environmental and security applications, such as applications in chemical sensing applications, propulsion systems for MEMS devices, self-destructing computer chips, or as tiny light sources that could be detected by infrared or night-vision camera equipment.

Embodiments of the invention may also be used in any application as an initiator where an explosion, deflagration, or fast reaction occurs. An embodiment of the invention is a solid-state explosive that includes porous silicon and a solid-state oxidant such as a nitrate salt, a perchlorate salt, a fluoride salt, or even conventional explosives such as PETN, metal azides and TNT. In accordance with the invention, components of the silicon-based explosive may be mixed prior to the desired moment of detonation, with an explosion only initiated by subsequent detonation.

The explosive preferably includes porous nanocrystalline silicon, which is particularly advantageous in that it can be incorporated into silicon-based microfabrication technologies, such as MEMS devices. While the porous nanocrystalline silicon may assume a variety of forms, one preferred form is a thin film electrochemically etched into a single crystal or polycrystalline silicon substrate. Other forms include porous silicon chemically etched into a single crystal or polycrystalline silicon substrate or into a powder of crystalline silicon particles. There is a premium on reliable and inexpensive initiators, and the silicon industry is optimal for such initiators insofar as silicon microfabrication technologies are reliable and highly amenable to mass production.

Additionally, the porous nanocrystalline silicon may serve as both the excitation source (via the explosion) and as the matrix for an analyte, which may be any number of substances, such as toxic heavy metal ions, which include lead, mercury, and cadmium. The surface area, porosity, and morphology of porous silicon can also be tailored to suit individual applications by altering etching conditions and a substrate, and the material can be patterned by simple photoelectrochemical or metal-assisted techniques. Suitable methods for tailoring the structure may be found in U.S. Pat. Nos. 6,248,539; 5,453,624; 5,338,415; and 5,318,676. These elements of control make explosive porous silicon useful in microarray analysis, as a "smart" ignition system for conventional explosives or as propulsion systems for MEMS.

Porous silicon provides a source of silicon nanowires, and porous silicon wafers may be saturated with various dopants to create practical and robust chemical sensors. Porous silicon can also be fabricated in multilayers so that a doped layer can change its optical properties in the presence of target chemicals relative to another layer to provide highly sensitive chemical detection. The instant invention contemplates, for example, a handheld sensor that can detect extremely small quantities of the nerve gas sarin.

In one embodiment of the instant invention, porous nanocrystalline silicon that includes a solid oxidant is used to create a silicon-based explosive. While the instant invention contemplates that a multitude of solid oxidants may be combined with porous nanocrystalline silicon to achieve a silicon-based explosive, the solid oxidant is preferably one of a nitrate salt, a perchlorate salt, a fluoride salt, or PETN, metal azides or TNT. Unlike the conventional oxidants used with silicon-based explosives, such as nitric acid and liquid oxygen, the solid oxidant of the instant invention enables a user to mix individual components of the silicon-based explosive prior to the desired moment of explosion.

More specifically, in an embodiment of the invention that includes a nitrate salt as the solid state oxidant, the nitrate salt used in combination with the porous nanocrystalline silicon is preferably selected from the group that includes the alkali metals and alkaline earth metals, such as sodium nitrate, potassium nitrate, ammonium nitrate, magnesium nitrate, or calcium nitrate. Gadolinium nitrate may also be used. In an embodiment wherein a perchlorate salt is selected to be the solid state oxidant, the perchlorate salt is preferably selected from the group consisting of sodium perchlorate, potassium perchlorate, or lithium perchlorate. Suitable fluoride salts for embodiments including fluoride salts as the solid state oxidant preferably include potassium fluoride, potassium hexafluorophosphate, sodium tetrafluoroborate. Additionally, many of the conventional secondary explosives used industrially, such as PETN, metal azides, TNT may likewise serve as the oxidant. Thus, the instant invention contemplates inclusion of a wide variety of solid state oxidants.

The nanocrystalline silicon is porous and behaves similarly to a sponge with nanometer-size holes. The solid state oxidant is absorbed into these holes, and may subsequently be baked into the nanocrystalline silicon. Preferably the oxidant may be placed into the pores from a solution containing the solid state oxidant. A solvent of the solution is allowed to evaporate at ambient temperatures or by mild (<120 deg C.) heating, leaving behind a deposit of the solid state oxidant within the pores of the porous silicon material. Turning now to an embodiment including a nitrate salt as the solid state oxidant, the nitrate salt, such as the exemplary potassium nitrate, is baked into the porous nanocrystalline silicon, which results in a system behaving in a chemically similar manner to gunpowder, which is finely ground carbon mixed with potassium nitrate and sulfur. Moreover, the energy generated by the system is generally similar to that generated by ordinary gunpowder on a pound-for-pound basis. Detonation may be effected by a plurality of methods, such as a heat-producing impact, a spark of electricity created by friction or circuitry within a silicon chip, a thermal pulse that can be obtained from a bridge wire or other resistive heating device, with a pulse of light that can be obtained from an infrared laser or concentrated sunlight, or other methods known by those of ordinary skill in the art. MEMS devices, with which the porous silicon-based explosive of the instant invention may operate, typically have plenty of electricity available to generate a spark.

Embodiments of the porous silicon-based explosives that include either a nitrate salt or a perchlorate salt are contemplated for use as initiator reactions in any device in which an explosion, deflagration or other fast reaction occurs. Other chemical oxidants, such as fluoride- or nitro-containing salts may be used insofar as the oxidant is preferably a chemical oxidant. For example, porous silicon, preferably in the form of a solid film, is combined with a nitrate salt or a perchlorate salt and may be used as a vehicle air bag actuator to initiate the inflation of an airbag. More specifically, a vehicle air bag's inflation system reacts sodium azide ($NaN_3$) with potassium nitrate ($KNO_3$) to produce nitrogen gas. Hot blasts of the nitrogen inflate the air bag. A porous silicon-based explosive that includes, for example, potassium nitrate, could be used to trigger the larger explosion of the azide salt that liberates the nitrogen.

For example, in conventional explosives, a typical bridge wire is a small strand of platinum or tungsten wire that is pressed into the explosive. When initiation is desired, a large current is caused to run through the bridge wire. The wire is heated until it reaches a threshold temperature that initiates the conventional explosive. However, because platinum and tungsten are relatively difficult to manufacture, many industries, such as the airbag industry, are moving towards cheaper, more reliable initiators. The instant invention therefore contemplates creating a bridge wire from silicon instead of platinum or tungsten, which could be used to give a silicon bridge wire extra energy. Additionally, if the silicon bridge wire were made to be porous nanocrystalline silicon in accordance with the invention, it may serve as an initiator without further modification, and could be pressed directly into the conventional explosive, scavenging the explosive's oxidant instead of requiring a separate source of potassium nitrate or other suitable oxidant.

Similarly, the porous silicon-based explosive of the instant invention that includes one of a nitrate salt, a perchlorate salt, a fluoride salt or other conventional solid state oxidant may be used as propulsion systems in MEMS devices. A molecule or other discrete unit of the explosive acts as a rocket for a MEMS device. Specifically, each MEMS device may include one or more tiny silicon-based explosive solid-fuel rocket engines that can be fired off individually by electronics. Such applications are useful, for example, in battlefield settings where the porous silicon-based explosive could be used as a propulsion system in a MEMS device. For example, small sensors could be dropped en masse from airplanes to monitor chemical and biological weapons deployment. The porous silicon-based explosive of the instant invention, used as a propulsion system, would permit those sensors to be mobile. The combination of porous silicon and oxidant would preferably be in the form of a cap, similar to a blasting cap or percussion cap used in bullets. Such an arrangement provides a convenient source of high temperature flame for flame ionization spectroscopy applications.

While the combination of porous nanocrystalline silicon and a solid state oxidant selected from one of a nitrate salt, a perchlorate salt, a fluoride salt or conventional oxidant is an advantageous candidate for propulsion systems, gadolinium nitrate in particular is a preferred candidate for chemical sensing applications. Other solid state oxidants are sufficiently explosive, but also include impurities that render the resultant flame difficult to analyze via spectrometry. For example, potassium nitrate includes impurities that cause a resulting flame to burn violet, making spectral analysis of trace analytes difficult. Moreover, potassium nitrate tends to cause moisture absorption from the ambient air, which decreases the efficacy and lifespan of the explosive.

The inherent purity of gadolinium nitrate therefore makes it an attractive alternative for embodiments used in chemical sensing applications, especially those where real-time chemical analysis in the field is desired. When gadolinium nitrate is baked into porous nanocrystalline silicon, the resulting mixture includes tiny channels having an increased surface area, which enhances the explosive nature of the mixture.

A common laboratory test method is to burn a sample of material and subsequently analyze the color of the flame via spectrometry, which indicates the presence of specific elements. When burned, gadolinium nitrate emits in the ultraviolet portion of the spectrum, therefore burning with no interfering spectral lines. Thus, if any coloration is perceived during the explosion of gadolinium nitrate, the coloration is due to the analyte(s). However, conventional processes require obtaining the test material and returning to lab to subsequently analyze the test material. In contrast, the instant invention contemplates using the porous silicon-based gadolinium nitrate explosive to generate tiny explosions that could provide a flame source for tiny handheld chemistry labs.

For example, the instant invention contemplates placing a piece of nanomaterial that includes the porous silicon-based explosive of the instant invention at a predetermined location suspected of containing an analyte, such as a field in close proximity to a suspect water source, such as a reservoir. A small amount of water is soaked up by the nanomaterial, such as from between 1 and 10 micro liters. The nanomaterial is then ignited in a "flame test", and the flame is the characteristic color of the elements contained within the sample. Preferably, the sample is ignited with a small filament of silicon or other metal that is resistively heated to incandescence. A photographic snapshot of the flame could be taken, and subsequently analyzed with a spectrometer. As illustrated in FIG. 1, a porous nanocrystalline substrate 10 having a solid state oxidant 12 bound thereto is placed in proximity to a location 14 suspected of containing an analyte 16 of interest. The analyte 16 is absorbed by the porous nanocrystalline substrate 10, and the mixture is subsequently detonated via one of a plurality of detonation methods, such as heat-producing impact, a spark of electricity created by friction or circuitry within a silicon chip, a thermal pulse that can be obtained from a bridge wire or other resistive heating device, with a pulse of light that can be obtained from an infrared laser or concentrated sunlight, or other methods known by those of ordinary skill in the art. A photograph of the resulting flame may be subjected to spectral analysis for detection of the analyte 16.

The instant invention also operates to detect an airborne analyte as well. To detect an airborne analyte that is in particulate or fog form, the nanomaterial is first exposed to a suspect location, and any ambient analyte adsorbs to a surface thereof and may be visually detected. Ambient analyte may be adsorbed from ambient liquid, gas or particulate matter. Detonation of the nanomaterial, either in a remote location or after it has been collected and returned to an analysis site, will create a flash of light that has a spectrum characteristic of the analyte. The resulting flame renders a visual indication of the presence of absence of an analyte. For example, the presence of sodium ions may be detected in this manner when the device is operated near a sea coast.

When silicon is electrochemically corroded in solutions containing hydrofluoric acid, a porous structure results. The pores propagate primarily in the direction of the crystal, and depending on the electrochemical current, the electrolyte composition, and the dopant characteristics of the wafer, the average diameter of the pores can be tuned from a few nanometers to several microns.

Porous silicon samples may be prepared by an electrochemical etch of silicon. A suitable etching solution is prepared by adding an equal volume of pure ethanol to an aqueous solution of HF (48% by weight). Silicon wafers may be cut to size and have specific portions exposed for etching. Electrical contact is made to the wafer to create etching current of sufficient density. To a first approximation, the etching time will determine the thickness of the porous thin film, while the current density controls pore size. Bragg reflectors are produced by modulating the current density periodically during the etch. After etching, porous thin films are rinsed. Porous thin films are preferably oxidized or otherwise chemically modified in an environment selected to immunize the films from being reactive to the types of sample to be tested.

Porous silicon samples were prepared from n-type (P-doped) silicon wafers with (100) orientation and resistivity of a 4 ohm/cm. Samples were etched in a 1:1 (v/v) solution of 49% aqueous HF/100% ethanol for 15 minutes at a constant current density of 50 mA/cm$^2$. A 300 W tungsten lamp adjusted to 50 mW/cm$^2$ provided front side illumination. The resulting porous layers were 1.2 cm in diameter and approximately 24 micrometers thick, with pore sizes up to 1 micrometer (as determined by scanning electron microscopy). After etching, the samples were rinsed with ethanol and hexane, dried under a stream of nitrogen, then cleaved into four equal sections. A dried section was covered with 10 micro liters of a 0.2 M solution of $Gd(NO_3)_3 \cdot 6H_2O$ in ethanol. Samples were allowed to dry in air for at least 1 hour. The nitrate-treated dried samples exploded when scratched with a diamond scribe or when subjected to a small electric spark.

A bright flash of light accompanies detonation of a typical sample, i.e., a square silicon wafer (2×2 cm$^2$) with a circular porous silicon film. Most porous silicon samples could be induced to explode, regardless of the type of crystalline silicon used (p- or n-type, high or low dopant density) or the resulting porous matrix morphology (micro porous to macro porous). Samples that contained a large amount of surface oxide (as determined by Fourier transform infrared spectroscopy, FTIR) were usually not explosive. As a result, freshly etched samples were used.

The explosive nature of a porous silicon/oxidizer mixture has been described previously. Addition of concentration nitric acid to freshly etch porous silicon was reported to produce a "flash of light with an audible pop." Similarly, addition of liquid $O_2$ to freshly etched porous Si can induce an explosion even at temperatures as low as 4.2 K. However, addition of the oxidizing agent as a dilute nitrate salt solution (instead of the liquid agents used previously) allows the preparation of a solid material that can be detonated in a more controlled fashion. Effectively, this combination is a silicon-based version of black powder, which is a mixture of potassium nitrate, sulfur and charcoal in the proportions 74.0%, 10.4%, and 15.6%. A simple thermodynamic calculation indicates that the enthalpy of reaction for the porous Si/nitrate material is approximately −1000 kcal/kg. This estimate is slightly larger than the values reported for the enthalpy of −850 kcal/kg, depending upon the exact formulation used.

Samples for atomic emission spectroscopy were added to the porous Si/nitrate matrix in either solution or solid form. If added in solution form, typically 10 micro liters of a 0.1 M solution of the analyte was used. Finely divided solids were slurried in ethanol or tetrahydrofuran (THF) and then spread onto the porous SI explosive matrix. Detonation was accomplished by discharge from a coil charged by a 9 V battery. The accompanying light emission was collected using a fiber optic probe and analyzed with an Ocean Optics SD2000 spectrometer. Spectra were not corrected for the wavelength dependent response of the detector/monochromator system. The identification of lines in the emission spectra was accomplished by comparison to literature values obtained from flame photometric analyses.

An emission spectrum was captured from a typical porous Si/nitrate explosion. Gadolinium does not have any significant atomic emission lines over the wavelength range studied (400-900 nm). A sharp peak observed at 589 nm was due to a sodium impurity, presumably from airborne contaminants. By the method of standard addition, the background sodium concentration was estimated to be between $10^{11}$ and $10^{12}$ atoms $cm^{-2}$. This estimate is in agreement with the sodium concentrations previously determined in HF-treated crystalline Si, reported to be $<4 \times 10^{11}$ $cm^{-2}$. Secondary ion mass spectrometry (SIMS) analyses of porous Si have yielded sodium levels as low as $10^6$ $cm^{-2}$ for micro porous samples (pore size <2 nm). The low levels reported in the literature were attributed to the small pore size excluding airborne sodium-containing particulates. Since the porous Si used in these explosion studies has much larger pores (up to 1 micrometer), size exclusion is not expected.

A comparison of the uncorrected explosion spectrum to an incandescent source of known color temperature (voltage-adjusted to match the explosion) was made. This temperature is similar to that achieved by air/natural gas (2000-2200 K) or air/acetylene (2300-2700K) flames used in atomic emission spectroscopy, particularly in flame photometric detection of alkali metals. Indeed, the presence of a sharp, atomic-like emission line in the spectrum confirms that he explosion generates sufficient energy. Emission spectra from porous silicon samples treated with different alkali metal salts have been observed, and render narrow atomic emission lines for the entire series. A peak at 589 nm appears in all the spectra because of the sodium contamination discussed above. Note also that spectra for heavier elements display lines due to lighter impurities: for example, the spectrum for rubidium nitrate displays peaks due to potassium and lithium. It was not determined whether this contamination was present in the reagents or due to exposure in a contaminated laboratory atmosphere.

Heavy metal elements were also detected. Observations of the explosion spectra from samples containing Ba, Sr, and Pb salts render lines from alkali metals, again presumably from airborne contaminants or impurities in the reagents. Peaks in the Ba and Sr spectra have been assigned in the literature as molecular emission lines. A doublet is assigned to a fluoride-containing Ba species. The analyte used was $BaF_2$. The two peaks are attributed to a hydroxide-containing Sr species that must have been generated in the flame, since the analyte was $Sr(NO_3)_2$. The peak indicated in the Pb spectra is the result of Pb atomic emission.

In the case of strongly emitting elements, quantitative analyses are possible. Porous Si/nitrate samples were treated with increasing amounts of potassium acetate in ethanol. Spectra were observed from explosions of porous Si/Gd $(NO_3)_3$ samples that were treated with ethanol solutions containing (from top to bottom) 2.0, 1.0, 0.50, and 0.25 nmol of $K(OOCCH_3)$. The spectra were corrected by first subtracting the broad white light emission and then normalizing to the intensity of the Na impurity. To account for variations in the excitation explosion, all spectra were normalized to the intensity of the unresolved Na doublet (589.0 and 589.6 nm.). A region of the emission spectra containing the most intense K lines is observed at 766.5 and 769.9 nm. The broad, white light background was subtracted from the emission spectra presented.

The intensity of the light emitted from (and the volume of) the porous silicon explosion was easily varied by changing the amount of added oxidant or adjusting the etching conditions. Qualitatively, increased nitrate levels produce a more intense explosion. Increasing the HF concentration of the etching solution (which decreases the porosity) also increases the intensity of the explosion. An HF/EtOH concentration of 3:1 produced an extremely bright flash and very loud explosion. A 1:1 ratio yielded a blast of moderate intensity. The 1:3 mixture was generally not explosive.

In conclusion, a simple method is presented for generating a solid-state explosive using porous silicon and a solid state oxidant. This material functions well as an alternative excitation source for atomic emission spectroscopy. The energy associated with the explosion is sufficient to excite atomic emission from the alkali metals and Pb, in addition to molecular emission from Ba and Sr. Both solution and solid analytes have been used. Qualitative analysis for K was demonstrated. The intensity of the explosion can be varied by adjusting the HF/EtOH ratio used in the preparation of the porous Si material. Explosive nitrate-treated porous silicon is a promising material for applications such as qualitative elemental analysis in microarrays or as propulsion sources in MEMS devices.

While various embodiments of the present invention have been shown and described, it should be understood that other modifications, substitutions and alternatives are apparent to one of ordinary skill in the art. Such modifications, substitutions and alternatives can be made without departing from the spirit and scope of the invention, which should be determined from the appended claims.

Various features of the invention are set forth in the following claims.

What is claimed is:

1. An initiator explosive device for detonating a second explosive comprising:
   porous nanocrystalline silicon; and
   a solid state oxidant nitrate salt disposed within pores of said porous nanocrystalline silicon, wherein said nitrate salt is selected from the group consisting of sodium nitrate, potassium nitrate, ammonium nitrate, magnesium nitrate, calcium nitrate, and gadolinium nitrate.

2. An initiator explosive device for detonating a second explosive comprising:
   porous nanocrystalline silicon; and
   a solid state oxidant disposed within pores of said porous nanocrystalline silicon, wherein said porous nanocrystalline silicon comprises a nanowire.

3. An initiator explosive device for detonating a second explosive comprising:
   porous nanocrystalline silicon; and
   an explosive solid state oxidant disposed within pores of said porous nanocrystalline silicon
   wherein said porous nanocrystalline silicon comprises a thin film, and wherein said solid state oxidant comprises a solid state oxidant selected from the group consisting of PETN, a metal azide, and TNT.

4. The explosive device of claim 3 wherein said solid-state oxidant is baked into the pores of said porous nanocrystalline silicon.

5. A method for detecting a target analyte comprising:
providing an initiator explosive device of nanocrystalline silicon having a plurality of pores disposed therein; and a solid state oxidant disposed within said pores;
igniting the porous nanocrystalline silicon containing the target analyte and the oxidant; and
measuring an emission spectrum for the presence of the target analyte.

6. The method of claim 5 further comprising providing a porous nanocrystalline silicon substrate in the form of a thin film.

7. The method of claim 5 further comprising selecting the oxidant to be gadolinium nitrate.

8. The method of claim 5 further comprising baking the oxidant with the nanocrystalline silicon so that the oxidant is baked into pores of the porous nanocrystalline silicon.

9. The method of claim 5 further comprising absorbing from between approximately 1 and 10 micro liters.

10. The method of claim 5 further comprising igniting by resistively heating a silicon filament.

11. The method of claim 5 further comprising photographing the emission spectra.

12. The method of claim 11 further comprising subjecting the photograph to spectrometry analysis.

13. The method of claim 5 further comprising absorbing a predetermined amount of a solution containing the target analyte on the porous nanocrystalline silicon.

14. The method of claim 5 further comprising absorbing a predetermined amount of ambient gas containing the target analyte on the porous nanocrystalline silicon.

15. The method of claim 5 further comprising absorbing a predetermined amount of ambient liquid containing the target analyte on the porous nanocrystalline silicon.

16. The method of claim 5 further comprising absorbing a predetermined amount of ambient particulate matter containing the target analyte on the porous nanocrystalline silicon.

* * * * *

UNITED STATES PATENT AND TRADEMARK OFFICE
CERTIFICATE OF CORRECTION

PATENT NO. : 7,942,989 B2
APPLICATION NO. : 10/731220
DATED : May 17, 2011
INVENTOR(S) : Sailor et al.

It is certified that error appears in the above-identified patent and that said Letters Patent is hereby corrected as shown below:

On the Title Page:

Item (56) under "Other Publications", Page 2, left column, line 2, delete "Uebowitz" and insert --Liebowitz-- therefor.

Item (56) under "Other Publications", Page 2, right column, line 4, delete "tomic emission icroscopy" and insert --atomic emission microscopy-- therefor.

| | |
|---|---|
| Col. 1, line 25 | After "invention" delete "including" and insert --include-- therefor. |
| Col. 1, line 47 | After "nitric acid" delete "with" and insert --which-- therefor. |
| Col. 6, line 37 | After "solution of" delete "$Gd(NO_3)_{3\square}$ $6H_2O$" and insert --$Gd(NO_3)_3 \cdot 6H_2O$-- therefor. |
| Col. 6, line 52 | Delete "concentration" and insert --concentrated-- therefor. |
| Col. 6, line 53 | Before "porous silicon" delete "etch" and insert --etched-- therefor. |
| Col. 7, line 39 | Before "explosion" delete "he" and insert --the-- therefor. |

In the Claims:

Col. 8, line 63
Claim 3, line 5   After "nanocrystalline silicon" insert a --;--.

Signed and Sealed this
Eleventh Day of October, 2011

David J. Kappos
*Director of the United States Patent and Trademark Office*